United States Patent [19]

Sick

[11] 4,302,105
[45] Nov. 24, 1981

[54] DETECTION APPARATUS FOR FINDING HOLES IN WEBS

[75] Inventor: Erwin Sick, Icking, Fed. Rep. of Germany

[73] Assignee: Erwin Sick GmbH, Optik-Elektronik, Waldkirch, Fed. Rep. of Germany

[21] Appl. No.: 12,045

[22] Filed: Feb. 14, 1979

[30] Foreign Application Priority Data

Feb. 27, 1978 [DE] Fed. Rep. of Germany ....... 2808359

[51] Int. Cl.³ .......................................... G01N 21/89
[52] U.S. Cl. .................................... 356/237; 250/224; 250/572; 350/171
[58] Field of Search ............................... 356/237–239, 356/380, 386, 387, 431, 430; 350/6.8, 6.9, 171, 169, 211; 250/224, 578, 572; 331/94.5 K

[56] References Cited

U.S. PATENT DOCUMENTS 4,011,857 3/1977 Rice ..................................... 350/211
4,127,771 11/1978 Sick ..................................... 250/221

FOREIGN PATENT DOCUMENTS 2532602 1/1977 Fed. Rep. of Germany ....... 360/6.8

Primary Examiner—John K. Corbin
Assistant Examiner—Bruce Y. Arnold

[57] ABSTRACT

Detection apparatus for finding holes in moving webs uses a row of individual mutually sideways displaced stepped mirror strips in combination with a scanning device which periodically scans a light beam from a laser over the individual mirrors of each strip, to generate a scanning light curtain directed at the surface of a web. A detection device comprising a row of individual Fresnel lenses and associated photoelectronic detectors is arranged parallel to the row of mirror strips to receive light transmitted through any hole present in the web. The individual Fresnel lenses focus any light received onto their associated photoelectric detectors the outputs from which signify the presence of the hole. Means are provided for introducing a degree of divergence into the beams deflected from the stepped mirrors and forming the light curtain whereby the light curtain scans across the web without gaps.

4 Claims, 3 Drawing Figures

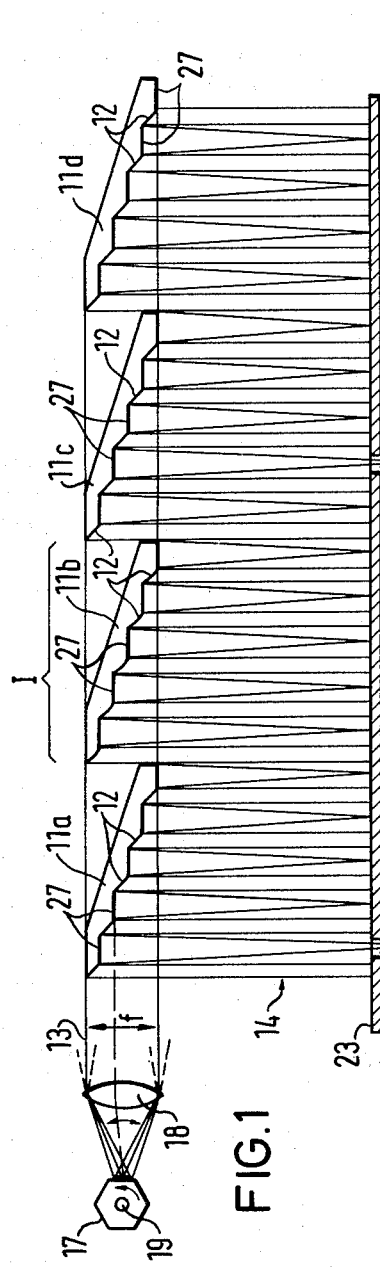
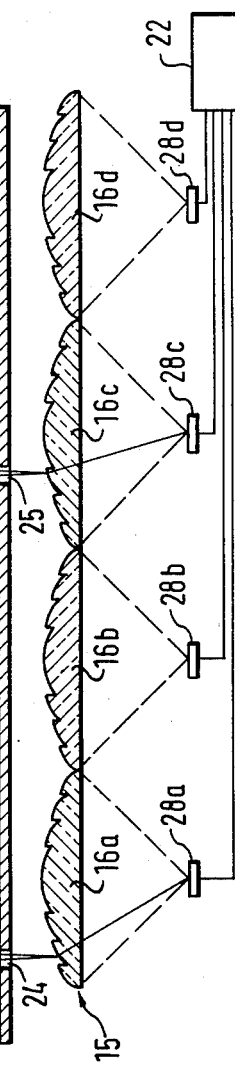
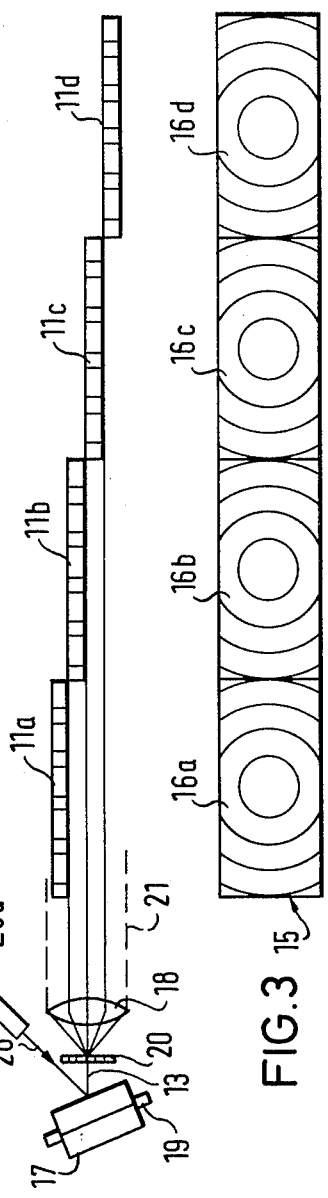
FIG.1
FIG.2
FIG.3

DETECTION APPARATUS FOR FINDING HOLES IN WEBS

The present invention relates to a detection apparatus for finding holes in moving webs of material and has particular reference to apparatus of the kind using a transmission device including a laser arranged in front of the web for generating a light curtain, and a detection device, formed by a row of lenses with photoelectric converters located therebehind, arranged behind the web and wherein the electrical output signals of the photoelectric converters are passed to an electronic processing device.

Numerous light curtains and grids of light barriers (e.g. DE-OS No. 1 616 016) are already available which are also suitable for finding holes in webs. The known apparatuses are, however, frequently so costly and need so much space that they are practically out of the question for finding holes.

A principal object of the present invention thus resides in providing a hole finding apparatus which through simple and uncomplicated construction and the capability of being manufactured economically is very compactly constructed but which, nevertheless, ensures a certain and error-free indication of the presence of a hole. At the same time it should also be possible, at least within certain limits, to allow also a coarse determination of the position of a hole in the web.

According to the present invention there is provided detection apparatus for finding holes in webs and having a transmission device including a laser arranged to direct a light curtain at a web, a detection device formed by a row of lenses with associated photoelectric converters located therebehind, disposed to receive light transmitted through any hole in the web and an electronic processing device for processing the electrical output signals of the photoelectric converters; said transmission device comprising a row of individual sideways displaced inclined stepped mirror strips, and a scanning device for directing a beam from said laser in the direction of the row to scan the individual mirrors one after the other, thereby deflecting the light through substantially 90° to form said light curtain and said detection device comprising a row of individual Fresnel lenses arranged edgewise one after the other and extending parallel to the row of strips.

In this manner a single light source and a single relatively narrow scanning region is sufficient in order to generate a very wide light curtain which corresponds to the width of the web and in which, on the detection size the cost and trouble is kept low through the use of economically manufacturable Fresnel lenses. The arrangement is constructionally very compact as the stepped mirror strips can be housed in a relatively narrow housing which extends along the light curtain whilst the row of Fresnel lenses likewise only needs to extend over the length and breadth of the region containing the light curtain. The photoelectric converters can be arranged at a very small distance from the Fresnel lenses.

It is important that the stepped mirror strips have such an inclination to the transmitted ray and such a step pitch that all regions of the web to be monitored are reached by reason of the natural scattering of the sharply defined transmitted light beam.

It is especially advantageous when the sharply defined laser beam is deflected onto a scanning device, such as a mirror wheel, if the reflecting surface of the scanning device is located at the focal point of a transmitting lens the diameter of which corresponds to the extent of the stepped mirror strips in the direction of the scanning movement of the beam transmitted from the lens.

In order to direct the sharply defined light rays one after the other onto the various stepped mirror strips the mirror wheel is, in accordance with a first embodiment, a Weiler type mirror wheel the individual mirror surfaces of which are so inclined at different angles to the rotational axis that the stepped mirror strips are scanned one after the other. This arrangement is particularly suitable for a hole finding apparatus as the transmitted light beam is only incident at any one time on a single mirror of the stepped mirror strips so that, by suitable coordination between the rotational movement of the mirror wheel and the electronic processing device, the location of the scanning light ray is fixed at any one moment and thus, if a hole is indicated, its position in the direction of scanning can be determined.

A particularly simple embodiment which is particularly suitable for hole finding is, however, characterized in that a screen of cylindrical lenses is arranged behind the mirror wheel, with the cylindrical lenses at right angles to the rotational axis, so as to fan out the sharply defined light ray only in a plane containing the rotational axis to form a light band which simultaneously strikes all the strips. In this embodiment a practically flat light band is present which simultaneously periodically scans all the stepped mirror strips. Periodic scanning light rays are thus simultaneously guided over as many individual regions of the web to be scanned as the number of stepped mirror strips that are provided. The individual scanning zones are thus relatively short so that for a specified scanning speed given by the rotational speed of the mirror wheel the individual regions of the web are more frequently swept over by the scanning ray. The web which in general is led past the light curtain with a specific speed can thus be moved at a larger speed without the danger that a hole in the web will pass unrecognized through the light curtain.

It is especially advantageous when one Fresnel lens is associated with each stepped mirror strip. In this embodiment each Fresnel lens could have its width exactly matched to the associated stepped mirror strip in which case the succeeding Fresnel lenses would have to be displaced analogously to the stepped mirror strips.

It is of particular advantage when from 5 to 20 and preferably 10 Fresnel lenses are provided for each meter of the row.

The invention will now be described by way of example only in the following and with reference to the drawing which shows:

FIG. 1 is a schematic side view of a hole detecting apparatus with a web provided in the light curtain, FIG. 2 is a schematic plan view of the subject of FIG. 1 and FIG. 3 is a plan view of the row of Fresnel lenses in accordance with FIG. 1.

In the drawings a transmission device includes a laser (not shown) for directing a laser beam 26 onto a scanning device in the form of a mirror wheel 17. Mirror wheel 17 is rotatable about an axis 19 to produce a scanning light ray 13 which is made parallel by a lens 18 and which periodically scans, in the sense shown by the double arrow f of FIG. 1, across a predetermined relatively narrow scanning region. The transmission device also incudes a row of individual inclined stepped mirror strips 11a, b, c, d arranged one behind the other and displaced sideways (as can be seen from FIG. 2) onto which the scanning device directs the beam from the laser. The scanning beam thus periodically scans the individual mirrors one after the other thereby deflecting the light from the stepped mirror strips to form a light curtain.

The individual stepped mirror strips each comprise individual mirrors 12 which deflect the transmitted ray 13 through 90° and non-reflecting regions 27 which extend parallel to the scanning light ray 13. Preferably a regularly alternating arrangement of mirrors 12 and non-reflecting regions 27 is present.

The unmirrored regions 27 can only be permitted to be of such a length in the direction of the scanning light ray 13 that a light curtain without gaps is generated in the region of the light curtain in which the web to be monitored is located. As can be seen from FIG. 1 one achieves a light curtain without gaps in the vicinity of the web 23 by reason of the natural scattering of the laser ray 13. For this purpose the web 23 to be monitored for holes 24, 25 must be removed at a sufficient distance from the stepped mirror strips 11 as is indicated in FIG. 1.

A row 15 of Fresnel lenses 16a, b, c, d which are cut to rectangular shapes and directly adjoin one another edgewise are located directly behind the web to be monitored for holes and which must be regarded as moving at right angles to the plane of the drawing in FIG. 1. The Fresnel lenses 16a, b, c and d concentrate the light which is incident on them e.g. through holes 24 or 25 onto photoelectric converters 28a, b, c, d. The photo-electric converters 28a, b, c, d are connected to an electronic processing circuit 22. The Fresnel lenses; their associated photo-electric converters and the processing circuit form a detection device which detects light transmitted through any holes in the web.

In order to be able to illuminate the individual stepped mirror strips 11a, b, c, d one after the other with the transmitted light beam, the mirror wheel 17 is, in accordance with a first embodiment, constructed as a so-called Weiler type mirror wheel. Preferably, however, a screen 20 of cylindrical lenses is arranged directly behind the mirror wheel 17 of FIG. 2 which so fans out the sharply defined laser beam 26 from a laser 26a, in the plane of FIG. 2 that a light band 21 exists behind the lens 18 which as per FIG. 1 simultaneously periodically scans all the stepped mirror strips 11 in the direction of the double arrow f. The light band 21 is shown in broken lines in FIG. 2.

The electronic processing circuit 22 can process the electrical output signals of the photoelectric converters 28a, b, c, d either separately or jointly. By joint processing an indication of the position of holes 24, 25 made recognizable by the device is foregone. The device has, however, in this case a very simple electronic construction.

Preferably the dead zones 27 between the individual mirrors 12 are bridged by generating an extended light bead on the mirror wheel 17 in the manner illustrated in FIG. 1 in place of a light point. As a result it is not an exactly parallel beam that emerges from the transmitting lens 18, which is preferably an objective lens, but rather a lightly diverging beam as is shown in broken lines and which results in the whole of the web 23 being detected by transmitted light.

A further possibility for ensuring a gapless monitoring of the web 23 is illustrated in the region I where the stepped mirror strip 11b is provided with lightly convexly curved individual mirrors 12. This arrangement could also be used for all the stepped mirror strips 11a to 11d in place of the somewhat scattered incident light beam.

It is generally convenient to provide from 5 to 20 and preferably to individual Fresnel lenses for each meter of width of the row.

It will be appreciated by those skilled in the art that certain further modifications may be made to the layout of the above described teaching. In particular it is contemplated that a mirror surface could be provided beneath the web and that the detection device could be arranged alongside the transmission device. In this embodiment the light curtain from the transmitting device would be directed at an angle to the surface of the web and light transmitted through holes in the web and specularly reflected at the mirror would be detected by the detection device. If necessary the processing circuit could be adapted to eliminate the effects of any non-specularly reflected light received by the detection device after reflection from the surface of the web.

I claim:

1. Detection apparatus for finding holes in webs and having a transmission device including a laser arranged to direct a light curtain at a web, a detection device including photoelectric detection means, disposed to receive light transmitted through holes in the web, and an electronic processing device for processing signals from said photo-electric detection means; said transmission device comprising a row of individual stepped mirror strips, each said strip being displaced sideways relative to the preceding strip of the row and being inclined to the direction of the row, and a scanning device for directing a beam from said laser in the direction of the row to scan the individual mirrors which are inclined relative to said beam one after the other thereby deflecting the light through substantially 90° to form said light curtain, said transmitting device further comprising optical means for introducing a degree of divergence into the beams deflected from said stepped mirror strips and forming said light curtain whereby said light curtain scans across said web without gaps, and said detection device comprising a row of individual Fresnel lenses, each said Fresnel lens having an operative section of substantially rectangular form for receiving light, and said Fresnel lenses being arranged edgewise one after the other in a substantially abutting relationship and extending parallel to the row of strips, together with a number of photoelectric converters defining said photoelectric detection means and being positioned to receive light from said Fresnel lenses.

2. Detection apparatus according to claim 1 in which said scanning device includes a mirror wheel and in which said optical means comprises an arrangement whereby the beam received on said stepped mirror strips from said mirror wheel is made slightly divergent in the plane of the row.

3. Detection apparatus according to claim 2 and in which the mirror wheel is a Weiler type mirror wheel, the individual mirror surfaces of which are so inclined at different angles to the rotational axis thereof that the stepped mirror strips are scanned one after the other.

4. Detection apparatus according to claim 1 and in which said optical means comprises an arrangement whereby the individual mirrors of said stepped mirror strip are made slightly convex.

* * * * *